(12) United States Patent
Albus et al.

(10) Patent No.: US 6,262,123 B1
(45) Date of Patent: Jul. 17, 2001

(54) ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

(75) Inventors: Udo Albus, Florstadt; Joachim Brendel, Bad Vilbel; Heinz-Werner Kleemann, Bischofsheim; Hans Jochen Lang, Hofheim; Wolfgang Scholz, Eschborn; Jan-Robert Schwark, Frankfurt; Andreas Weichert, Egelsbach, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/398,196

(22) Filed: Sep. 17, 1999

Related U.S. Application Data

(63) Continuation of application No. 09/080,227, filed on May 18, 1998, now abandoned, which is a continuation of application No. 08/808,284, filed on Feb. 28, 1997, now abandoned.

(30) Foreign Application Priority Data

Mar. 4, 1996 (DE) .............................. 196 08 161

(51) Int. Cl.⁷ ..................... A61K 31/165; A61K 31/155; C07C 279/20
(52) U.S. Cl. ............. 514/617; 514/307; 514/311; 514/357; 546/145; 546/175; 546/329; 564/170; 564/176
(58) Field of Search ................ 514/614, 617, 514/618, 634, 307, 311, 357; 564/147, 162, 170, 176, 177; 546/145, 175, 329

(56) References Cited

U.S. PATENT DOCUMENTS

| | | | |
|---|---|---|---|
| 5,461,066 | * 10/1995 | Gericke et al. | 514/329 |
| 5,571,842 | 11/1996 | Kleenman et al. | 514/618 |
| 5,670,544 | 9/1997 | Weichert et al. | 514/618 |
| 5,679,712 | 10/1997 | Schwark et al. | 514/621 |
| 6,001,881 | * 12/1999 | Weichert et al. | 514/620 |

FOREIGN PATENT DOCUMENTS

| | | |
|---|---|---|
| 44 21 495 | 12/1995 | (DE) . |
| 44 30 213 | 2/1996 | (DE) . |
| 0 612 723 | 8/1994 | (EP) . |
| 0 640 588 | 1/1995 | (EP) . |
| 0 699 666 | 3/1996 | (EP) . |
| 0 743 301 | 11/1996 | (EP) . |
| 0 760 365 | 3/1997 | (EP) . |

* cited by examiner

*Primary Examiner*—Shailendra Kumar
(74) *Attorney, Agent, or Firm*—Finnegan, Henderson, Farabow, Garrett and Dunner, L.L.P.

(57) ABSTRACT

Ortho-substituted benzoylguanidines of the formula I

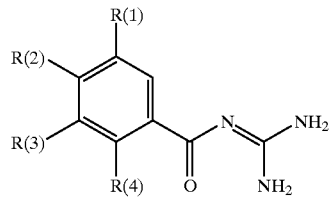

in which R(1) to R(4) have the meanings given in the claims, are suitable, as antiarrhythmic pharmaceuticals having a cardioprotective component, for the prophylaxis and treatment of infarction and for the treatment of angina pectoris. They also inhibit, in a preventive manner, the pathophysiological processes associated with the genesis of ischemically induced damage, in particular associated with the triggering of ischemically induced cardiac arrhythmias.

23 Claims, No Drawings

ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

This is a continuation of application Ser. No. 09/080,227, filed May 18, 1998, now abandoned which is a continuation of application Ser. No. 08/808,284, filed Feb. 28, 1997, now abandoned, which are incorporated herein by reference.

DESCRIPTION

The invention relates to benzoylguanidines of the formula I

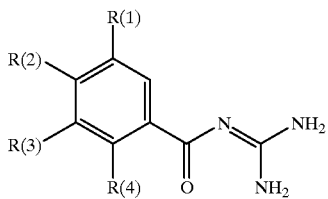

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S or NR(5),
a is zero or 1;
b is zero, 1 or 2;
c is zero, 1, 2 or 3;
R(5) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatic radicals phenyl, biphenylyl or naphthyl are unsubstituted or substituted by 1–3 substituents selected from the group consisting of F, Cl, CF$_3$ methyl, methoxy and NR(7)R(8);
R(7) and R(8) are, independently, H or alkyl having 1, 2, 3 or 4 carbon atoms; or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF$_3$, CH$_3$ methoxy, hydroxyl, amino, methylamino and dimethylamino;
f is zero, 1 or 2;
R(11) and R(12) are, independently of each other, defined as R(10), or hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked by a C atom or an N atom of the ring,
which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18) or —C[R(20)R(21)]$_k$—(CO)—[(CR(22)R(23)]$_l$—R(24),
k is zero, 1, 2, 3 or 4;
l is zero, 1, 2, 3 or 4;
R(13) and R(14) are, identically or differently, —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
R(17) is hydrogen or methyl,
g, h and i are, identically or differently, zero, 1, 2, 3 or 4;
j is 1, 2, 3 or 4;
R(15) and R(16) are, identically or differently, hydrogen, alkyl having 1, 2, 3, 4, 5 or 6 carbon atoms, or are, together with the carbon atom carrying them, cycloalkyl having 3, 4, 5, 6, 7 or 8 carbon atoms;
R(18) is phenyl,
which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms;
or
R(18) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(18) is cycloalkyl having 3, 4, 5, 6, 7 or 8 carbon atoms;
R(19), R(20), R(21), R(22) and R(23) are, identically or differently, hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
one of the two substituents R(2) and R(3) is hydroxyl; and
the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, CN, I or —(CH$_2$)$_n$—(CF$_2$)$_o$—CF$_3$;
n is zero or 1;
o is zero or 1;
and the pharmaceutically tolerated salts thereof.
Compounds of the formula I are preferred in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CF$_2$)$_c$—CF$_3$;
x is oxygen;
a is zero or 1;
c is zero, 1, 2 or 3;
or
R(1) is —SR(10) or —OR(10);
R(10) is —C$_f$H$_{2f}$-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF$_3$, CH$_3$, methoxy, hydroxyl, amino, methylamino and dimethylamino;

f is zero or 1;

or

R(1) is phenyl, naphthyl, biphenylyl or heteroaryl having 1, 2, 3, 4, 5, 6, 7, 8 or 9 carbon atoms, with the latter being linked via a C atom or N atom of the ring, which are unsubstituted or substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —C≡CR(18) or —C[R(19)]═CHR(18);

R(13) and R(14) are, identically of differently, —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);

R(17) is hydrogen or methyl, g, h and i are, identically or differently, zero, 1 or 2;

is 1 or 2;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or substituted as phenyl;

or

R(18) is alkyl having 1, 2, 3, 4, 5 or 6 carbon atoms, which is unsubstituted or substituted by 1–3 OH;

or

R(18) is cycloalkyl having 3, 4, 5, 6, 7 or 8 carbon atoms;

R(19) is hydrogen or methyl;

one of the substituents R(2) and R(3) is hydroxyl; and the other of the substituents R(2) and R(3) in each case is defined as R(1);

R(4) is alkyl having 1 or 2 carbon atoms, methoxy, F, Cl, Br, CN or —(CH$_2$)$_n$—(CF$_2$)$_o$—CF$_3$;

n is zero or 1;

o is zero or 1 and the pharmaceutically tolerated salts thereof.

Compounds of the formula I are very particularly preferred in which:

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or —Xa—(CF$_2$)$_c$—CF$_3$;

X is oxygen;

a is zero or 1;

c is zero or 1;

or

R(1) is —SR(10) or —OR(10);

R(10) is cycloalkyl having 4, 5 or 6 carbon atoms, or phenyl, where phenyl is unsubstituted or substituted by 1–3 substituents selected from the group consisting of F, Cl, CF$_3$, CH$_3$, methoxy, hydroxyl, amino, methylamino and dimethylamino;

or

R(1) is quinolyl, isoquinolyl or pyridyl, which are linked via a C atom or N atom of the ring; and which are unsubstituted or substituted by 1–3 substituents selected from the group consisting of F, Cl, CF$_3$, CH$_3$, methoxy, hydroxyl, amino, methylamino and dimethylamino, or R(1) is phenyl, which is unsubstituted or substituted by 1–3 substituents selected from the group consisting of F, Cl, CF$_3$, CH$_3$, methoxy, hydroxyl, amino, methylamino and dimethylamino, or R(1) is —C≡CR(18);

R(18) is phenyl or cycloalkyl having five or 6 carbon atoms;

one of the two substituents R(2) and R(3) is hydroxyl;

and the other of the substituents R(2) and R(3) in each case is defined as R(1);

R(4) is methyl, methoxy, F, Cl or CF$_3$;

and the pharmaceutically tolerated salts thereof.

Compounds of the formula I are especially preferred in which

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or CF$_3$;

one of the substituents R(2) and R(3) is hydroxyl, and the other of the substituents R(2) and R(3) in each case is defined as R(1);

R(4) is methyl, methoxy, F, Cl or CF$_3$;

and the pharmaceutically tolerated salts thereof.

A special preference is given to the compounds of the formula I which are selected from the group consisting of 2,6-dichlorobenzoylguanidine hydrochloride, 3-chloro-2,6-dimethoxybenzoylguanidine hydrochloride, 4-hydroxy-2,3,5,6-tetrafluorobenzoylguanidine hydrochloride, 4-hydroxy-2,5-trifluoromethylbenzoylguanidine hydrochloride and 4-hydroxy-2-methyl-5-trifluoromethylbenzoylguanidine hydrochloride.

Heteroaryl having 1, 2, 3, 4, 5, 6, 7, 8 or 9 carbon atoms is understood to mean radicals which are derived from phenyl or naphthyl, in which one or more CH groups are replaced by N and/or in which at least two adjacent CH groups are replaced by S, NH or O (with the formation of a five-membered aromatic ring). Furthermore, one or both atoms of the fusion site of bicyclic radicals can also be N atoms (as in indolizinyl).

Furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl; in particular furanyl, thienyl, pyrrolyl, imidazolyl, pyrazolyl, triazolyl, thiazolyl, pyridyl, indolyl, quinolyl and isoquinolyl, are, in particular, regarded as being heteroaryl having 1, 2, 3, 4, 5, 6, 7, 8 or 9 carbon atoms.

If one of the substituents R(1) to R(4) contains one or more centers of asymmetry, these centers can be either in the S or the R configuration. The compounds can be present as optical isomers, as diastereomers, as racemates or as mixtures thereof.

The designated alkyl radicals can be straight-chain or branched.

The invention furthermore relates to a process for preparing the compound I, which comprises reacting a compound of the formula II

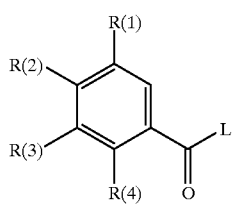

II in which R(1) to R(4) have the given meaning and L is a leaving group which can readily be substituted nucleophilically, with guanidine.

The activated acid derivatives of the formula II, in which L is an alkoxy group, preferably a methoxy group, a phenoxy group, a phenylthio group, a methylthio group or a 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II (L=Cl), other activated acid derivatives of the formula II can also be prepared, in a manner known per se, directly from the underlying benzoic acid derivatives (formula II, L=OH), such as the methyl esters of the formula II, in which L=OCH$_3$, by treating with gaseous HCl in methanol, the imidazolides of the formula II by treating with carbonyidi-imidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, in addition to which there is also the activation of benzoic acids with dicyclohexylcarbodiimide (DCC) or with O-[(cyano(ethoxycarbonyl)methylen) amino]-1,1,3,3-tetramethyluronium tetrafluoroborate ("TOTU")[Weiss and Krommer, Chemiker Zeitung 98, 817 (1974)]. A series of suitable methods for preparing activated carboxylic acid derivatives of the formula II are given, with citation of the source literature, in J. March, Advanced Organic Chemistry, Third Edition (John Wiley & Sons, 1985), p. 350.

An activated carboxylic acid derivative of the formula II is reacted with guanidine, in a manner known per se, in a protic or aprotic, polar but inert organic solvent. In this context, methanol, isopropanol or THF, at a temperature of from 20° C. up to the boiling temperature of these solvents, have proved to be of value when reacting the methyl benzoates (II, L≦OMe) with guanidine. Most reactions of compounds II with salt-free guanidine were advantageously carried out in aprotic, inert solvents such as THF, dimethoxyethane or dioxane. However, if a base, such as NaOH, is used, water can also be employed as a solvent when reacting II with guanidine.

If L=Cl, the reaction is advantageously carried out in the presence of an added acid-capturing agent, for example in the form of excess guanidine, for the purpose of removing the hydrohalic acid.

Some of the underlying benzoic acid derivatives of the formula II are known and described in the literature. The unknown compounds of the formula II can be prepared using methods which are known from the literature. The resulting benzoic acids are converted into novel compounds I using one of the above described process variants.

The introduction of some substituents in the 2, 3, 4 and 5 positions is achieved using methods, which are known from the literature, of the palladium-mediated cross-coupling of aryl halides or aryl triflates with, for example, organostannanes, organoboronic acids or organoboranes or organocopper compounds or organozinc compounds.

In general, benzoylguanidines I are weak bases and can bind acid with the formation of salts. Salts of all the pharmacologically tolerated acids, for example halides, in particular hydrochlorides, lactates, sulfates, citrates, tartrates, acetates, phosphates, methylsulfonates and p-toluenesulfonates, are suitable for use as acid addition salts.

The compounds I are substituted acylguanidines.

Compounds which are similar to the compounds I are known from European Laid-Open Specification 612 723 A 1 (HOE 93/F 054). While these disclosed compounds already contain hydroxyl groups as substituents in the phenyl nucleus, they do not contain any substituents in the ortho position.

The novel compounds differ from the known compounds in exhibiting an extraordinarily high activity in the inhibition of Na$^+$/H$^+$ exchange and in exhibiting improved solubility in water.

Like the known compounds, they do not have any undesirable and disadvantageous salidiuretic properties.but nevertheless exhibit very good antiarrhythmic properties, as are important, for example, for treating diseases which occur in association with symptoms of oxygen deficiency. As a consequence of their pharmacological properties, the compounds are outstandingly suitable, as antiarrhythmic pharmaceuticals having a cardioprotective component, for the prophylaxis and treatment of infarction and for treating angina pectoris, in association with which they also inhibit, or greatly diminish, in a preventive manner, the pathophysiological processes associated with the genesis of ischemically induced damage, in particular associated with the triggering of ischemically induced cardiac arrhythmias. On account of their protective effects against pathological hypoxic and ischemic situations, the novel compounds of the formula I can, as a consequence of their inhibition of the cellular Na$^+$/H$^+$ exchange mechanism, be used as pharmaceuticals for treating all acute or chronic damage which is provoked by ischemia, or diseases which are primarily or secondarily induced thereby. This relates to their use as pharmaceuticals for surgical interventions, for example in organ transplantations, where the compounds can be used both for protecting the organs in the donor before and during removal, for protecting removed organs, for example when treating them with, or storing them in, physiological bathing fluids, and also when transferring them into the recipient. The compounds are likewise valuable pharmaceuticals, having a protective effect, for use when carrying out angioplastic surgical interventions, for example on the heart and also on peripheral blood vessels. In conformity with their protective effect against ischemically induced damage, the compounds are also suitable for use as pharmaceuticals for treating ischemias of the nervous system, in particular of the CNS, in association with which they are suitable, for example, for treating stroke or cerebral edema. In addition to this, the novel compounds of the formula I are also suitable for treating forms of shock such as allergic, cardiogenic, hypovolemic and bacterial shock.

The novel compounds of the formula I are also notable for exhibiting a strong inhibitory effect on the proliferation of cells, for example fibroblast cell proliferation and proliferation of the smooth muscle cells of the blood vessels. For this reason, the compounds of the formula I are suitable for use, as valuable therapeutic agents, for diseases in which cell proliferation constitutes a primary or secondary cause, and can therefore be used as antiatherosclerotics and as agents against late complications in diabetes, cancerous diseases, fibrotic diseases, such as pulmonary fibrosis, hepatic fibrosis or renal fibrosis, and organ hypertrophies and hyperplasias, in particular in hyperplasia or hypertrophy of the prostate.

The novel compounds are effective inhibitors of the cellular sodium/proton antiporter ($Na^+/H^+$ exchanger), which, in numerous diseases (essential hypertension, atherosclerosis, diabetes, etc.), is also elevated in cells, such as erythrocytes, thrombocytes or leukocytes, which are readily accessible for measurement. The novel compounds are therefore suitable for use as simple and outstandingly good scientific tools, for example in their use as diagnostic agents for identifying and differentiating particular forms of hypertension and also of atherosclerosis, diabetes, proliferative diseases, etc. In addition to this, the compounds of the formula I are suitable for preventive therapy, to prevent the genesis of high blood pressure, for example the genesis of essential hypertension.

In this context, pharmaceuticals which comprise a compound I can be administered orally, parenterally, intravenously, rectally or by inhalation, with the preferred mode of administration depending on the particular clinical picture of the disease. In this context, the compounds I can be used either alone or together with pharmaceutical auxiliary substances, both in veterinary medicine and in human medicine.

Based on his specialist knowledge, the skilled person is familiar with the auxiliary substances which are suitable for the desired pharmaceutical formulation. For example, antioxidants, dispersants, emulsifiers, defoamers, taste corrigents, preservatives, solubilizers or dyes can be used in addition to solvents, gelatinizing agents, suppository bases, tablet auxiliary substances and other active compound excipients.

For an oral use form, the active compounds are mixed with the additives, such as carrier substances, stabilizers or inert diluents, which are suitable for the purpose and brought, using the customary methods, into the administration forms, such as tablets, coated tablets, hard gelatin capsules or aqueous, alcoholic or oily solutions, which are suitable. Gum arabic, magnesium hydroxide, magnesium carbonate, potassium phosphate, lactose, glucose or starch, in particular corn starch, can, for example, be used as inert excipients. In this context, the preparation can be effected either as a dry granulate or as a wet granulate. Examples of suitable oily carrier substances or solvents are vegetable or animal oils, such as sunflower oil or cod liver oil.

For subcutaneous or intravenous administration, the active compounds are brought, if desired together with the substances which are suitable for the purpose, such as solubilizers, emulsifiers or other auxiliary substances, into solution, suspension or emulsion. Examples of suitable solvents are: water, physiological sodium chloride solution or alcohols, for example ethanol, propanol or glycerol, and also sugar solutions, such as glucose or mannitol solutions, or else a mixture composed of the different solvents mentioned.

Solutions, suspensions or emulsions of the active compound of the formula I in a pharmaceutically harmless solvent, such as, in particular, ethanol or water, or a mixture of these solvents, are, for example, suitable for use as a pharmaceutical formulation for administration in the form of aerosols or sprays.

If required, the formulation can also comprise other pharmaceutical auxiliary substances as well, such as surfactants, emulsifiers and stabilizers, and also a propellant gas. Such a preparation customarily comprises the active compound in a concentration of from about 0.1 to 10, in particular of from about 0.3 to 3%, by weight.

The dose of the active compound of the formula I to be administered, and the frequency of administration, depend on the strength and duration of the effect of the compounds employed; they also depend on the nature and severity of the disease to be treated and on the sex, age, weight and individual responsiveness of the mammalian subject to be treated.

On average, the daily dose of a compound of the formula I in the case of a patient of about 75 kg in weight is at least 0.001 mg/kg, preferably 0.01 mg/kg, up to at most 10 mg/kg, preferably 1 mg/kg, of body weight. In the case of acute attacks of the disease, for example immediately after suffering a cardiac infarction, even higher, and in particular more frequent, doses may also be necessary, for example up to 4 individual doses per day. Up to 200 mg per day may be necessary in the case of i.v. use, in particular, for example in the case of an infarction patient in intensive care.

List of abbreviations:

| | |
|---|---|
| MeOH | methanol |
| DMF | N,N-dimethylformamide |
| RT | room temperature |
| EA | ethyl acetate (EtOAc) |
| m.p. | melting point |
| THF | tetrahydrofuran |
| eq. | equivalent |

Experimental part

General protocol for preparing benzoylguanidines (I)

Variant A: From benzoic acids (II, L=OH)

1.0 eq. of the benzoic acid derivative of the formula II is dissolved or suspended in anhydrous THF (5 ml lmmol), and 1.1 eq. of carbonyldiimidazole are then added. After stirring at RT for 2 hours, 5.0 eq. of guanidine are introduced into the reaction solution. After this mixture has been stirred overnight, the THF is distilled off under reduced pressure (rotary evaporator), water is added, the pH of the mixture is adjusted to from 6 to 7 with 2N HCl and the corresponding benzoylguanidine (formula I) is filtered off. The benzoylguanidines which are obtained in this way can be converted into the corresponding salts by treating them with aqueous, methanolic or ethereal hydrochloric acid or other pharmacologically tolerated acids.

General protocol for preparing benzoylguanidines (I)

Variant B: From alkyl benzoates (II, L≦O-alkyl)

1.0 eq. of the alkyl benzoate of the formula II and 5.0 eq. of guanidine (free base) are dissolved in isopropanol or suspended in THF and heated to boiling until conversion is complete (monitoring by thin layer chromatography) (typical reaction time, from 2 to 5 h). The solvent is distilled off under reduced pressure (rotary evaporator) and the residue is taken up in EA and this solution is washed 3 × with a solution of $NaHCO_3$. It is then dried over $Na_2SO_4$ and the solvent is distilled off in vacuo; the residue is chromatographed on silica gel using a suitable eluent, for example EA/MeOH 5:1.

(Salt formation, cf. variant A)

EXAMPLE 1

2-Chloro4-hydroxybenzoylguanidine hydrochloride
Colorless crystals, m.p. 247° C. from 2-chloro -4-hydroxybenzoic acid in accordance with variant A.

EXAMPLE 2

2-Chloro-4-hydroxy-5-iodobenzoylguanidine hydrochloride Colorless crystals, m.p. 246–47° C.

Synthesis route:

a) Methyl 2-chloro -4-hydroxybenzoate from 2-chloro -4-hydroxybenzoic acid by esterification, at RT and within the space of 24 h, with methanol (excess) in the presence of 10 equivalents of acetyl chloride. Following aqueous working-up, crystallization takes place from ether/cyclohexane, colorless crystals, m.p. 128–30° C.

b) Methyl 2-chloro-4-hydroxy-5-iodobenzoate from a) by reaction, at RT and within the space of 1.5 h, with a mixture of 1.1 equivalents of N-chlorosuccinimide and 2.1 equivalents of potassium iodide in the presence of 10 equivalents of sodium acetate in half-concentrated glacial acetic acid. Aqueous working-up and column chromatography using cyclohexane/ethyl acetate 9:1 yields the desired product as a colorless solid, m.p. 191–92° C., and also methyl 2-chloro -460 4-hydroxy-3,5-diiodobenzoate as a colorless solid, m.p. 131–32° C.

c) 2-Chloro-4-hydroxy-5-iodobenzoylguanidine hydrochloride from methyl 2-chloro-4-hydroxy-5-iodobenzoate (cf. 2 b) in accordance with variant B.

EXAMPLE 3

2-Chloro4-hydroxy-3,5-diiodobenzoylguanidine hydrochloride Colorless solid, m.p. 205–10° C. (Decomposition) from methyl 2-chloro4-hydroxy-3,5-diiodobenzoate (cf. 2 b) in accordance with process B.

EXAMPLE 4

2-Chloro4-hydroxy-5-trifluoromethylbenzoylguanidine hydrochloride Colorless solid, amorphous, $(M+H)^+$: 282

Synthesis route:

a) Methyl 2-chloro -4-benzyloxy-5-iodobenzoate from methyl 2-chloro -4-hydroxy-5-iodobenzoate by reaction, at 80° C. and within the space of 3 h, with 1.1 equivalents of benzyl bromide in the presence of potassium carbonate in DMF. Following aqueous working-up, recrystallization takes place from isopropanol, colorless crystals, m.p. 102–08° C.

b) Methyl 2-chloro -4-benzyloxy-5-trifluoromethylbenzoate from 4 a) by heating at 160° C. with 2 equivalents of potassium trifluoroacetate in N-methyl-2-pyrrolidinone in the presence of copper(I) iodide within the space of 5 h. Aqueous working-up and column chromatography using cyclohexane/ethyl acetate 9:1 yields colorless crystals, m.p. 126–27° C.

c) 2-Chloro -4-benzyloxy-5-trifluoromethylbenzoylguanidine from 4 b) in accordance with process B without salt formation, colorless crystals, m.p. 180° C.

d) 2-Chloro -4-hydroxy-5-trifluoromethylbenzoylguanidine hydrochloride from 4 c) by means of hydrogenation using palladium/charcoal and subsequent hydrochloride formation, colorless solid, amorphous, $(M+H)^+$: 282.

EXAMPLE 5

4-Hydroxy-2,5-trifluoromethylbenzoylguanidine hydrochloride: Colorless crystals, m.p. 211° C.

Synthesis route:

a) Methyl 4-benzyloxy-2,5-trifluoromethylbenzoate from 4 b) by means of analogous trifluoromethylation but at an elevated temperature (180° C.) and with a reaction time of 5 h, colorless crystals, m.p. 11 6° C.

b) 4-Benzyloxy-2,5-trifluoromethylbenzoylguanidine hydrochloride from 5 a) in accordance with the general protocol, colorless crystals, m.p. 221° C.

c) 4-Hydroxy-2,5-trifluoromethylbenzoylguanidine hydrochloride from 5 b) by means of hydrogenation on 10% palladium/charcoal in methanol at RT.

EXAMPLE 6

4-Hydroxy-2-methyl-5-trifluoromethylbenzoylguanidine hydrochloride:

Amorphous solid.

Synthesis route:

a) Methyl 2-methyl-4-benzyloxy-5-trifluoromethylbenzoate from methyl 2-chloro-4-benzyloxy-5-trifluoromethylbenzoate (4 b) via cross-coupling with 1.2 equivalents of methylzinc chloride (from methylmagnesium chloride by transmetallation with zinc(II) chloride/THF complex) by stirring at 80° C. in DMF in the presence of catalytic quantities of palladium(II) acetate and copper(I) iodide, colorless crystals, m.p. 105° C.

b) 4-Benzyloxy-2-methyl-5-trifluoromethylbenzoylguanidine hydrochloride from 6 a) in accordance with the general protocol, colorless crystals, m.p. 255° C.

c) 4-Hydroxy-2-methyl-5-trifluoromethylbenzoylguanidine hydrochloride from 6 b) in analogy with 5 c).

Pharmacological data

Inhibition of the rabbit erythrocyte $Na^+/H^+$ exchanger New Zealand White rabbits (Ivanovas) were given a standard diet containing 2% cholesterol for six weeks in order to activate the $Na^+/H^+$ exchange and thereby render it possible to use flame photometry to determine the $Na^+$ influx into the erythrocytes by way of $Na^+/H^+$ exchange. The blood was withdrawn from the aural arteries and rendered incoagulable by adding 25 IU of potassium heparin. One part of each sample was used for determining the hematocrit in duplicate by means of centrifugation. Aliquots of in each case 100 µl were used for measuring the initial $Na^+$ content of the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl) aminomethane). After that, the erythrocytes were washed three times with an ice-cold solution of MgCl$_2$/ouabain (mmol/l: 112 MgCl$_2$, 0.1 ouabain) and hemolyzed in 2.0 ml of distilled water. The intracellular sodium content was determined by flame photometry.

The net influx of Na$^+$ was calculated from the difference between the initial sodium values and the sodium content of the erythrocytes after incubation. The amiloride-inhibitable sodium influx was obtained from the difference in the sodium content of the erythrocytes after incubating with and without 3×10$^{-4}$ mol/l amiloride. The same procedure was adopted in the case of the novel compounds.

Results
Inhibition of the Na$^+$/H$^+$ exchanger:

| Example | IC$_{50}$(mol/l) |
|---|---|
| 1 | 4.0 × 10$^{-6}$ |
| 2 | 0.24 × 10$^{-6}$ |
| 3: | 0.10 × 10$^{-6}$ |
| 4: | 0.14 × 10$^{-6}$ |

What is claimed is:

1. An ortho-substituted benzoylguanidine of the formula I

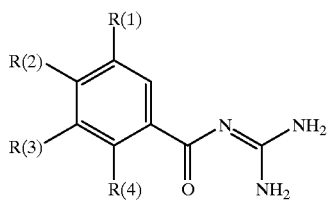

in which:
R(1) is H, F, Cl, Br, I, CN, NO$_2$, alkyl, having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S or NR(5),
a is zero or 1;
b is zero, 1 or 2;
c is zero, 1, 2or 3;
R (5) is H, alkyl having 1, 2, 3 or 4 carbon atoms or —C$_d$H$_{2d}$R($^6$);
d is zero, 1, 2, 3 or 4;
R(6) is cycloalkyl having 3, 4, 5, 6, 7 or 8 carbon atoms, phenyl, biphenylyl or naphthyl,
where the aromatic radicals phenyl, biphenylyl or naphthyl are unsubstituted or substituted by 1–3 substituents selected from the group consisting of F, Cl, CF$_3$, methyl, methoxy and NR(7)R(8);
R(7) and R(8) are, independently, H or alkyl having 1, 2, 3 or 4 carbon atoms;
or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF$_3$, CH$_3$, methoxy, hydroxyl, amino, methylamino and dimethylamino;
f is zero, 1 or 2;

R(11) and R(12) are, independently of each other, defined as R(10), or hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked by a C atom or an N atom of the ring, which are in each case unsubstituted or substituted by 1–3 substituents selected from the group consisting of F, Cl, CF$_3$, CH$_3$, methoxy, hydroxyl, amino, methylamino and dimethylamino,
or
R(1) is —SR(13),—OR(13),—NHR(13),—NR(13)R (14),—CHR(13)R(15), —C[R(15)R(16)OH], —C≡CR(18), —C[R(19)]=CHR(18) or —C[R(20)R (21)]$_k$—(CO)—[(CR(22)R(23)]$_l$—R(24),
k is zero, 1, 2, 3 or 4;
l is zero, 1, 2, 3 or 4;
R(13) and R(14) are, identically or differently, —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
R(17) is hydrogen or methyl,
g, h and i are, identically or differently, zero, 1, 2, 3 or 4;
is 1, 2, 3 or 4;
R(15) and R(16) are, identically or differently, hydrogen, alkyl having 1, 2, 3, 4, 5 or 6 carbon atoms, or are, together with the carbon atom carrying them, cycloalkyl having 3, 4, 5, 6, 7 or 8 carbon atoms;
R(18) is phenyl, which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms;
or
R(18) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(18) is cycloalkyl having 3, 4, 5, 6, 7 or 8 carbon atoms;
R(19), R(20), R(21), R(22) and R(23) are, identically or differently, hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R($^{18}$);
m is 1, 2, 3 or 4;
one of the two substituents R(2) and R(3) is hydroxyl; and
the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, CN, I or —(CH$_2$)$_n$—(CF$_2$)$_o$—CF$_3$;
n is zero or 1;
o is zero or 1;
or a pharmaceutically tolerated salts thereof.

2. A compound of the formula I as claimed in claim 1, wherein:
R(1) is H, F, Cl, Br, I, CN, NO2, alkyl, having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CF$_2$)$_c$—CF$_3$;

X is oxygen;

a is zero or 1;

c is zero, 1, 2 or 3;

or

R(1) is —SR(10) or —OR(10);

R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, $CF_3$, $CH_3$, methoxy, hydroxyl, amino, methylamino and dimethylamino;

f is zero or 1;

or

R(1) is phenyl, naphthyl, biphenylyl or heteroaryl having 1, 2, 3, 4, 5, 6, 7, 8 or 9 carbon atoms, with the latter being linked via a C atom or N atom of the ring, which are unsubstituted or substituted by 1–3 substituents selected from the group consisting of F, Cl, $CF_3$, $CH_3$, methoxy, hydroxyl, amino, methylamino and dimethylamino, or R(1) is —SR(13), —OR(13), —NHR(13), —NR(13)R(14),—C≡CR(18) or —C[(R(19)]=CHR(18);

R(13) and R(14) are, identically of differently, —$(CH_2)_g$—$(CHOH)_h$—$(CH_2)_i$—$(CHOH)_j$—R(17) or —$(CH_2)_g$—O—$(CH_2-CH_2O)_h$—R(24);

R(17) is hydrogen or methyl, g, h and i are, identically or differently, zero, 1 or 2;

is 1 or 2;

R(18) is phenyl, which is unsubstituted or substituted by 1–3 substituents selected from the group consisting of F, Cl, $CF_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or substituted as phenyl;

or

R(18) is alkyl having 1, 2, 3, 4, 5 or 6 carbon atoms, which is unsubstituted or substituted by 1–3 OH;

or

R(18) is cycloalkyl having 3, 4, 5, 6, 7 or 8 carbon atoms;

R(19) is hydrogen or methyl;

one of the substituents R(2) and R(3) is hydroxyl;

and the other of the substituents R(2) and R(3) in each case is defined as R(1);

R(4) is alkyl having 1 or 2 carbon atoms, methoxy, F, Cl, Br, CN or —$(CH_2)_n$—$(CF_2)_o$—$CF_3$;

n is zero or 1;

o is zero or 1.

3. A compound of the formula I as claimed in claim 1, wherein:

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or —$X_a$—$(CF_2)_c$—$CF_3$;

X is oxygen;

a is zero or 1;

c is zero or 1;

or

R(1) is —SR(10) or —OR(10);

R(10) is cycloalkyl having 4, 5 or 6 carbon atoms, or phenyl, where phenyl is unsubstituted or substituted by 1–3 substituents selected from the group consisting of F, Cl, $CF_3$, $CH_3$, methoxy, hydroxyl, amino, methylamino and dimethylamino;

or

R(1) is quinolyl, isoquinolyl or pyridyl, which are linked via a C atom or N atom of the ring;

and which are unsubstituted or substituted by 1–3 substituents selected from the group consisting of F, Cl, $CF_3$, $CH_3$, methoxy, hydroxyl, amino, methylamino and dimethylamino, or R(1) is phenyl, which is unsubstituted or substituted by 1–3 substituents selected from the group consisting of F, Cl, $CF_3$, $CH_3$, methoxy, hydroxyl, amino, methylamino and dimethylamino, or R(1) is —C≡CR(18);

R(18) is phenyl or cycloalkyl having five or 6 carbon atoms;

one of the two substituents R(2) and R(3) is hydroxyl;

and the other of the substituents R(2) and R(3) in each case is defined as R(1);

R(4) is methyl, methoxy, F, Cl or $CF_3$;

and the pharmaceutically tolerated salts thereof.

4. A compound of the formula I as claimed in claim 1, wherein:

R(1) is H, F, Cl, an alkyl having 1, 2, 3 or 4 carbon atoms, an alkoxy having 1, 2, 3 or 4 carbon atoms, a cylcoalkyl having 5 or 6 carbon atoms, a cycloalkoxy having 5 or 6 carbon atoms or $CF_3$;

one of the substituents R(2) and R(3) is hydroxyl, and the other of the substituents R(2) and R(3) in each case is defined as R(1); and R(4) is methyl, methoxy, F, Cl or $CF_3$.

5. A compound according to claim 1 which is 2-chloro-4-hydroxybenzoylguanidine or a pharmaceutically tolerable salt thereof.

6. A compound according to claim 1 which is 2-chloro-4-hydroxy-5-iodobenzoylguanidine or a pharmaceutically tolerable salt thereof.

7. A compound according to claim 1 which is 2-chloro-4-hydroxy-3,5-diiodobenzoylguanidine or a pharmaceutically tolerable salt thereof.

8. A compound according to claim 1 which is 2-chloro-4-hydroxy-3,5-diiodobenzoylguanidine or a pharmaceutically tolerable salt thereof.

9. A compound according to claim 1 which is 4-hydroxy-5-trifluoromethylbenzoylguanidine or a pharmaceutically tolerable salt thereof.

10. A compound according to claim 1 which is 4-hydroxy-2-methyl-5-trifluoromethylbenzoylguanidine or a pharmaceutically tolerable salt thereof.

11. A method of treating or preventing diseases which are brought about by ischemic conditions in a patient comprising administering to the patient a therapeutically effective amount of a compound according to claim 1.

12. A method of treating or preventing cardiac infarction in a patient comprising administering to the patient a therapeutically effective amount of a compound according to claim 1.

13. A method of treating or preventing angina pectoris in a patient comprising administering to the patient a therapeutically effective amount of a compound according to claim 1.

14. A method of treating or preventing ischemic conditions of the heart in a patient comprising administering to the patient a therapeutically effective amount of a compound according to claim 1.

15. A method of treating or preventing ischemic conditions of the peripheral and central nervous system and stroke in a patient comprising administering to the patient a therapeutically effective amount of a compound according to claim 1.

16. A method of treating or preventing ischemic conditions of peripheral organs and limbs in a patient comprising administering to the patient a therapeutically effective amount of a compound according to claim 1.

17. A method of treating shock conditions in a patient comprising administering to the patient a therapeutically effective amount of a compound according to claim 1.

18. A method of preparing a patient for a surgical operation or an organ transplantation comprising administering to the patient a therapeutically effective amount of a compound according to claim 1.

19. A method of preparing a medicament for the preservation and storage of transplants for surgical procedures comprising administering to the transplant a therapeutically effective amount of a compound according to claim 1.

20. A method of treating diseases in which cell proliferation constitutes a primary or secondary cause in a patient comprising administering to the patient a therapeutically effective amount of a compound according to claim 1.

21. The method according to claim 20, wherein the diseases in which cell proliferation constitutes a primary or secondary cause are atherosclerosis, complications of diabetes, cancerous diseases, fibrotic diseases, or prostate hyperplasia.

22. The method according to claim 21, wherein said fibrotic diseases are pulmonary fibrosis, hepatic fibrosis or renal fibrosis.

23. A pharmaceutical composition comprising an effective amount of a compound according to claim 1 in admixture with a physiologically acceptable carrier.

* * * * *

UNITED STATES PATENT AND TRADEMARK OFFICE
CERTIFICATE OF CORRECTION

PATENT NO. : 6,262,123 B1
DATED : July 17, 2001
INVENTOR(S) : Albus et al.

It is certified that error appears in the above-identified patent and that said Letters Patent is hereby corrected as shown below:

Column 11,
Line 48, "R($^6$)" should read -- R(6) --.

Column 12,
Line 16, "[(CR" should read -- [CR --.
Line 25, insert "j" before "is".
Line 48, "R($^{18}$)" should read -- R(18) --.
Line 63, "N02" should read -- N0$_2$ --.

Column 13,
Line 25, "C[(R" should read -- C[R --.
Line 31, insert -- j -- before "is"

Signed and Sealed this

Ninth Day of July, 2002

Attest:

Attesting Officer

JAMES E. ROGAN
*Director of the United States Patent and Trademark Office*